(12) United States Patent
Lambert et al.

(10) Patent No.: US 9,364,461 B2
(45) Date of Patent: Jun. 14, 2016

(54) PROCESS FOR MANUFACTURING OPHTHALMIC OIL-IN-WATER EMULSIONS

(75) Inventors: Gregory Lambert, Chatenay-Malabry (FR); Frederic Lallemand, Fresnes (FR); Laura Rabinovich-Guilatt, Kadima (IL); Pascal Candillon, Massy (FR); Julien Lafosse, Ris-Orangis (FR)

(73) Assignee: SANTEN SAS, Evry (FR)

( * ) Notice: Subject to any disclaimer, the term of this patent is extended or adjusted under 35 U.S.C. 154(b) by 1837 days.

(21) Appl. No.: 11/962,324

(22) Filed: Dec. 21, 2007

(65) Prior Publication Data

US 2008/0181867 A1 Jul. 31, 2008

Related U.S. Application Data

(60) Provisional application No. 60/876,200, filed on Dec. 21, 2006.

(51) Int. Cl.
*A61K 9/00* (2006.01)
*A61K 31/415* (2006.01)
*A61K 9/107* (2006.01)

(52) U.S. Cl.
CPC .............. *A61K 31/415* (2013.01); *A61K 9/0048* (2013.01); *A61K 9/1075* (2013.01)

(58) Field of Classification Search
None
See application file for complete search history.

(56) References Cited

U.S. PATENT DOCUMENTS

| 5,496,811 | A | * | 3/1996 | Aviv et al. ........................ 514/78 |
| 5,698,219 | A | * | 12/1997 | Valdivia et al. ............... 424/450 |
| 5,817,254 | A | | 10/1998 | Wadle et al. |
| 6,007,826 | A | * | 12/1999 | Benita et al. .................. 424/401 |
| 6,153,657 | A | | 11/2000 | Kisuno et al. |
| 6,245,349 | B1 | * | 6/2001 | Yiv et al. ........................ 424/450 |
| 2004/0043043 | A1 | | 3/2004 | Schlyter et al. |
| 2005/0059583 | A1 | * | 3/2005 | Acheampong et al. ......... 514/11 |
| 2005/0118254 | A1 | | 6/2005 | Choi et al. |
| 2006/0204468 | A1 | | 9/2006 | Allef et al. |
| 2007/0264349 | A1 | * | 11/2007 | Lee et al. ...................... 424/489 |
| 2009/0220558 | A1 | | 9/2009 | Malotky |

FOREIGN PATENT DOCUMENTS

| EP | 0696452 | A1 | 4/1996 |
| EP | 0844001 | A1 | 5/1998 |
| JP | H0899867 | A | 4/1996 |
| JP | 2001157835 | A | 6/2001 |
| JP | 2005523261 | A | 8/2005 |
| WO | 9929316 | A1 | 6/1999 |
| WO | 03063826 | | 8/2003 |
| WO | 03063826 | A2 | 8/2003 |
| WO | 2006009112 | A1 | 1/2006 |
| WO | 2006050836 | A2 | 5/2006 |
| WO | 2006050837 | A2 | 5/2006 |
| WO | 2006107330 | A1 | 10/2006 |
| WO | 2007106213 | A2 | 9/2007 |

OTHER PUBLICATIONS

Kiang, Shmuel et al., Influence of Emulsion Droplet Surface Charge on Indomethacin Ocular Tissue Distribution, 2000, Pharmaceutical Development and Technology, vol. 5, No. 4, pp. 521-532.*
Siebenbrodt et al., "Poloxamer-Systems as Potential Ophthalmics II. Microemulsions", European Journal of Pharmaceutics and Biopharmaceutics 39 Feb. 1993, No. 1, p. 25-30.
Written Opinion of the International Searching Authority, dated Jun. 24, 2009, from corresponding application PCT/EP2007/064489.

* cited by examiner

*Primary Examiner* — Nannette Holloman
(74) *Attorney, Agent, or Firm* — Young & Thompson (57) ABSTRACT

The present invention relates to new processes for the preparation of oil-in-water emulsions useful in ophthalmic applications. In particular, processes are provided that include preparing a pre-concentrate of the oil-in-water emulsion, and diluting the pre-concentrate obtained to form the desired oil-in-water emulsion. The present invention also provides pharmaceutical compositions comprising an oil-in-water emulsion prepared by an inventive process, and methods of using these compositions for the treatment of an eye disease or condition.

25 Claims, 3 Drawing Sheets

PROCESS FOR MANUFACTURING OPHTHALMIC OIL-IN-WATER EMULSIONS

RELATED APPLICATION

This application claims priority to Provisional Patent Application Ser. No. 60/876,200 filed on Dec. 21, 2006 and entitled "Process for Manufacturing Large Volumes of an Ophthalmic Oil-in-water Emulsion". This Provisional Application is incorporated herein by reference in its entirety.

BACKGROUND OF THE INVENTION

Oil-in-water emulsions are widely used in ophthalmic products. Typical preparations of oil-in-water emulsions involve dissolving water-soluble components in an aqueous phase and dissolving oil-soluble components in an oil phase. The oil phase is then vigorously dispersed into the aqueous phase, for example, by mixing at several thousand revolutions per minute (r.p.m) for minutes to several hours. This process is called emulsification. Emulsification is an energy-consuming process, in which thermal and kinetic energies are invested in order to disperse the oil phase into numerous droplets of very small size but having a large total surface area.

Ocular comfort is of critical importance for commercial success in ophthalmic products. Emulsions containing a high concentration of oil (i.e., generally more than 6% v/v oil) are way too uncomfortable to be suitable for ophthalmic uses. Therefore, the ophthalmic industry produces highly diluted oil-in-water emulsions.

Producing large volumes of diluted ophthalmic oil-in-water emulsions requires significant investment in capital equipment, and is both time and energy consuming. Emulsifying large batch sizes requires very high energy input, as only a small amount of the invested energy is actually used to emulsify the oil, the major part of the energy being dissipated in the large volume of aqueous phase. Moreover, yields of emulsification are generally not optimal.

For large volumes, this above-described suboptimal process results in very long emulsification procedures with a potential negative impact on the chemical stability of emulsion components.

Therefore, there is still a need in the art for new approaches for the preparation of oil-in-water emulsions for ophthalmic applications. Particularly desirable is the development of processes of preparation that overcome the above-mentioned problems and limitations associated with currently used processes.

SUMMARY OF THE INVENTION

The present invention relates to an improved strategy for the preparation of ready-to-dilute oil-in-water emulsions. In particular, methods of preparation are provided that can be performed using equipments suitable for small to medium batch sizes. Compared to currently available processes, the methods provided herein exhibit satisfactory yields, require limited amounts of energy, and reasonable processing times.

More specifically, the present invention relates to processes for manufacturing ophthalmic oil-in-water microemulsions or submicroemulsions. Such processes generally comprise steps of: (1) manufacturing a pre-concentrate of an emulsion, and (2) diluting said pre-concentrate emulsion with a diluting aqueous solution to obtain the desired oil-in-water emulsion.

According to an embodiment of the invention, the pre-concentrate is in the form of an emulsion, which may be a cationic emulsion, an anionic emulsion or a non-ionic emulsion. In certain preferred embodiments, a pre-concentrate of the present invention is a cationic emulsion pre-concentrate.

Processes according to the present invention aim at manufacturing thermodynamically stable oil-in-water microemulsion or submicroemulsions containing dispersed droplets, preferably having a mean size generally of more than about 10 nm and less than about 500 nm. For example, the mean size of the droplets may be of more than about 10 nm and less than about 300 nm, preferably less than about 200 nm.

In certain preferred embodiments, microemulsions or submicroemulsions obtained using a process of the present invention are stable over periods of time in excess of about 12 months, preferably in excess of about 24 months, more preferably in excess of about 36 months.

In another aspect, the present invention relates to processes for manufacturing pre-concentrates of ophthalmic oil-in-water emulsions, preferably of ophthalmic oil-in-water microemulsions or submicroemulsions. Such processes generally comprise a step of emulsifying an oil phase with an aqueous phase and at least one surface-active agent to obtain a pre-concentrate of an oil-in-water emulsion. A pre-concentrate prepared by such a process generally has a content in oil that is higher than the content in oil of the final oil-in-water emulsion prepared by dilution of the pre-concentrate. According to a preferred embodiment, a pre-concentrate of the present invention is not suitable for direct administration to the eye of a patient, but becomes suitable for ophthalmic use after dilution.

More specifically, in processes of the present invention, a pre-concentrate of a desired oil-in-water emulsion is produced by emulsifying an oil phase comprising at least one oil that is suitable for ophthalmic use, with an aqueous phase and at least one surfactant. Oils that are suitable for ophthalmic use include, for example, castor oil, MCT, vegetal oils, mineral oils, and any combinations of these oils that are suitable for administration to the eye. In certain embodiments, the average hydrophilic-lipophilic balance (HLB) of the surface-active agent(s) is advantageously substantially equal to the HLB or average HLB emulsion requirement of the oil or oils of the oil phase used in the preparation process.

In certain embodiments, the oil phase may comprise one or more pharmaceutically active substances, including pro-drugs. For example, pharmaceutically active substances may be selected from the group consisting of antibiotics, antiviral agents, antifungals, intraocular pressure lowering agents, anti-inflammatory agents, steroids, anti-allergic compounds, anti-angiogenic compounds, biological agents, immuno-modulating agents, cytostatics, antioxidants, UV-filter compounds, fatty acids, and the like.

An advantage of the processes provided by the present invention is that they allow production of large volumes of emulsions without having to scale-up the emulsifying step.

In another aspect, the present invention relates to processes for preparing a desired ophthalmic oil-in-water emulsion by diluting a pre-concentrate obtained as described above. Such processes include diluting one volume of a pre-concentrate with 2 to 50 volumes of a diluting aqueous solution, such that the resulting ophthalmic oil-in-water emulsion has a content in oil of 5% v/v or less, preferably of 3% v/v or less, more preferably of 2% v/v or less, even more preferably of 1% v/v or less. Preferably, dilution is performed using 2 volumes of diluting aqueous solution for 1 volume of the pre-concentrate. More preferably, dilution is performed using 10 volumes of diluting aqueous solution for 1 volume of the pre-concentrate.

One advantage of such inventive processes is that oil-in-water emulsions obtained by dilution of pro-concentrates are formed with a lower energy input than that required in currently used processes.

In certain embodiments, the diluting aqueous solution comprises surfactants and/or additives, e.g., tonicity agents, viscosifying agents, buffering agents, preservatives, antioxidants, colorants or a micellar solution. Alternatively or additionally, the diluting aqueous solution comprises benzalkonium chloride. Alternatively or additionally, the diluting aqueous solution comprises one or more water-soluble therapeutic agent.

In another aspect, the present invention provides pre-concentrates of ophthalmic oil-in-water emulsions prepared by an inventive process. In the context of the present invention, a pre-concentrate is defined as an emulsion which may form a diluted emulsion by dilution which may form an emulsion (e.g., a microemulsion or submicroemulsion) by dilution in an aqueous medium, preferably on dilution of 1:1 to 1:50 (v/v), more preferably on dilution of 1:2 to 1:10 (v:v). Thus, a pre-concentrate may be in a liquid form or in a gel form, or in any form suitable in view of its further dilution in an aqueous medium. A pre-concentrate in the meaning of this invention is an emulsion comprising a content in oil higher than the content in oil of the final ophthalmic oil-in-water emulsion. In certain embodiments, a pre-concentrate of an ophthalmic oil-in-water emulsion is not suitable for administration to a patient.

In certain embodiments, a pre-concentrate of the present invention comprises droplets having a size substantially equal to the size to the final ophthalmic oil-in-water emulsion droplet size, e.g., greater than about 10 nm and less than about 500 nm, less than about 300 nm, or preferably less than about 200 nm, preferably less than about 150 nm, typically less than about 100 nm.

In certain embodiments, a pre-concentrate of the present invention is stable for periods of time in excess of 24 hours, preferably in excess of 3 days, more preferably in excess of 7 days.

In another aspect, the present invention provides ophthalmic oil-in-water emulsions obtained by dilution of a pre-concentrate as described herein.

In another aspect, the present invention provides pharmaceutical compositions comprising an effective amount of an oil-in-water emulsion prepared according to an inventive process disclosed herein.

In yet another aspect, the present invention relates to the use of an oil-in-water emulsion prepared according to an inventive process disclosed herein for the manufacture of a medicament for the treatment of an eye disease or condition. In a related aspect, the present invention also relates to medicament comprising an oil-in-water emulsion prepared according to an inventive process disclosed herein.

In still another aspect, the present invention provides methods for the treatment of an eye disease or condition in a subject. Such methods generally comprise a step of administering to the subject an effective amount of an ophthalmic oil-in-water emulsion prepared by an inventive process described herein. Administration may be by topical, intraocular or periocular routes. Such methods may be used to treat any eye disease or condition such as, for example, glaucoma, ocular inflammatory conditions such as keratitis, uveitis, intra-ocular inflammation, allergy, and dry eye syndrome ocular infections, ocular allergies, ocular infections, cancerous growth, neo-vessel growth originating from the cornea, retinal oedema, macular oedema, diabetic retinopathy, retinopathy of prematurity, degenerative diseases of the retina (macular degeneration, retinal dystrophies), and retinal diseases associated with glial proliferation.

These and other objects, advantages and features of the present invention will become apparent to those of ordinary skill in the art having read the following detailed description of the preferred embodiments.

DEFINITIONS

For purpose of convenience, definitions of a variety of terms used throughout the specification are presented below.

The term "ophthalmic", as used herein in connection with a composition or emulsion, refers to a composition or emulsion intended to be administered to the eye of a subject and which presents a pharmaceutical effect.

The terms "subject" and "individual" are used herein interchangeably. They refer to a human or another mammal (e.g., mouse, rat, rabbit, dog, cat, cattle, swine, sheep, horse or primate) that can be afflicted with or is susceptible to an eye disease or condition but may or may not have the disease or condition. In many embodiments, the subject is a human being. The terms "individual" and "subject" do not denote a particular age, and thus encompass adults, children, and newborns.

The term "eye disease or condition" refers to any of a wide variety of ocular conditions such as glaucoma, ocular inflammatory conditions such as keratitis, uveitis, ocular inflammation, post-surgical inflammation, allergy and dry eye syndrome ocular infections, ocular allergies, ocular infections, cancerous growth, neo vessel growth originating from the cornea, retinal oedema, macular oedema, diabetic retinopathy, retinopathy of prematurity, degenerative diseases of the retina (macular degeneration, retinal dystrophies), retinal diseases associated with glial proliferation, and the like.

The term "treatment" is used herein to characterize a method or process that is aimed at (1) delaying or preventing the onset of a disease or condition (in particular an eye disease or condition); (2) slowing down or stopping the progression, aggravation, or deterioration of the symptoms of the disease or condition; (3) bringing about amelioration of the symptoms of the disease or condition; or (4) curing the disease or condition. A treatment may be administered prior to the onset of the disease or condition, for a prophylactic or preventive action. Alternatively or additionally, a treatment may be administered after initiation of the disease or condition, for a therapeutic action.

A "pharmaceutical composition" is defined herein as comprising an effective amount of an inventive ophthalmic emulsion, and at least one pharmaceutically acceptable carrier or excipient.

As used herein, the term "effective amount", refers to any amount of a compound, agent or composition that is sufficient to fulfill its intended purpose(s), e.g., a desired biological or medicinal response in a tissue, system or subject. For example, in certain embodiments of the present invention, the purpose(s) may be: to slow down or stop the progression, aggravation, or deterioration of the symptoms of an eye disease or condition, to bring about amelioration of the symptoms of the disease or condition, and/or to cure the disease or condition. Determination of an effective amount is well within the ordinary skill in the art of pharmaceutical sciences and medicine, in that it may depend on various biological factors or individual variations and response to treatments.

The term "pharmaceutically acceptable carrier or excipient" refers to a carrier medium which does not interfere with the effectiveness of the biological activity of the active ingredient(s) and which is not excessively toxic to the host at a concentration at which it is administered. The term includes solvents, dispersion media, antibacterial and antifungal agents, isotonic agents, adsorption delaying agents, and the like. The use of such media and agents for pharmaceutically active substances is well known in the art (see, for example, "*Remington's Pharmaceutical Sciences*", E. W. Martin, 18$^{th}$ Ed., 1990, Mack Publishing Co.: Easton, Pa., which is incorporated herein by reference in its entirety).

The terms "therapeutic agent", "drug", and "pharmaceutically active substance" are used herein interchangeably. They refer to a substance, molecule, compound, agent, factor or composition effective in the treatment of a disease or condition.

The term "prodrug" has herein its art understood meaning and refers to a pharmaceutically inactive compound that acts as a drug precursor which, following administration, is converted to and/or releases the pharmaceutically active drug. Conversion or release may occur via a chemical or physiological process (e.g., upon being brought to a physiological pH or through enzyme activity). Conversion or release may occur prior to, during, or following adsorption, or at a specific target site of the body.

The terms "approximately" and "about", as used herein in reference to a number, generally includes numbers that fall within a range of 10% in either direction of the number (greater than or less than the number) unless otherwise stated or otherwise evident from the context (except where such a number would exceed a possible value).

The term "topical", when used herein to characterize the delivery, administration or application of a composition of the present invention, is meant to specify that the composition is delivered, administered or applied directly to the site of interest (i.e., to the eye) for a localized effect. Topical administration may be effected without any significant absorption of components of the composition into the subject's blood stream (to avoid a systemic effect). Alternatively, topical administration may lead to at least some absorption of components of the composition into the subject's blood stream.

The terms "surface-active agent" and "surfactant" are used herein interchangeably. They have their art understood meaning and refer to agents that lower the surface tension of a liquid, allowing easier spreading, and/or that lower the interfacial tension between two liquids. Surfactants are generally organic compounds that are amphipathic (i.e., they contain both hydrophobic groups—called tails—and hydrophilic groups—called heads).

DETAILED DESCRIPTION OF CERTAIN PREFERRED EMBODIMENTS

As mentioned above, the present invention relates to processes for the preparation of oil-in-water emulsions that have the advantage of producing emulsions suitable for use in ophthalmic applications with satisfactory yields and in reasonable times, and that can be performed using equipment small to medium batch sizes.

I—Processes for the Preparation of Ophthalmic Oil-in-water Emulsions

Processes provided by the present invention generally comprise steps of: (1) manufacturing a pre-concentrate of an oil-in-water emulsion, and (2) diluting the pre-concentrate obtained in step (1) with a diluting aqueous phase to obtain an oil-in-water emulsion that can be used in ophthalmic applications.

A. Pre-concentrates of Oil-in-Water Emulsions and Preparation Thereof

Methods of manufacturing a pre-concentrate of an oil-in-water emulsion according to the present invention generally comprise a step of emulsifying an oil phase with an aqueous phase and at least one surface-active agent to obtain the pre-concentrate. In such methods, the oil phase comprises at least one oil suitable for ophthalmic use.

In the methods of the present invention, the step of emulsification may be performed by any suitable method including, but not limited to, methods using colloid mills, rotor/stator homogenizers, high pressure homogenizers, and sonicating homogenizers. In general, the emulsifying step requires an energy input lower than required in methods currently used for the preparation of a diluted ophthalmic oil-in-water emulsions. In certain embodiments, the emulsifying step requires an energy input which is between about 2 and about 50 times lower than that required in currently available methods. For example, the energy input may be between about 2 and about 10 times lower, between about 5 and about 25 times lower, or between about 10 and about 50 times lower.

Oils suitable for ophthalmic use include, but are not limited to, castor oil, MCT, mineral oils, vegetal oils, and any combinations of these oils that are well tolerated at the eye level. As used herein, the term "MCT" refers to medium chain triglycerides. Medium chain triglycerides generally have a high solubility in water, are not significantly susceptible to oxidation, and are well suited for ophthalmic applications. Examples of vegetal oils include, but are not limited to, cotton seed, ground nut, corn, germ, olive, palm, soybean, and sesame oils. Examples of mineral oils include, but are not limited to, silicone and paraffin.

Methods of the present invention yields a pre-concentrate having a content in oil of between about 3% and about 50% v/v. For example, in certain embodiments, methods of the present invention yields a pre-concentrate having a content in oil of between about 6% and about 30% v/v. In other embodiments, methods of the present invention yields a pre-concentrate having a content in oil of between about 10% and about 20% v/v.

In methods of the present invention, the step of emulsification which leads to the formation of, a pre-concentrate is performed in the presence of an oil phase, an aqueous phase, and at least one surface-active agent (or surfactant). Surfactants suitable for use in processes of the present invention may be non-ionic surfactants, cationic, surfactants, or anionic surfactants. Examples of non-ionic surfactants that can be used in processes of the present invention include, but are not limited to, poloxamers, tyloxapol, polysorbates (e.g., polysorbate 80), polyoxyethylene castor oil derivatives, derivatives of cremophors (e.g., cremophor EL, and cremophor RH), sorbitan esters, polyoxyl stearates, cremophors (e.g., cremophor EL, and cremophor RH), and combinations thereof. Examples of cationic surfactants that are suitable for use in the present invention include, but are not limited to, $C_{10}$-$C_{24}$ primary alkylamines, tertiary aliphatic amines, quaternary ammonium compounds selected from the group comprising lauralkonium halide, cetrimide, hexadecyl-trimethylammonium halide, tetradecyltrimethyl-ammonium halide, dodecyltrimethyl-ammonium halide, cetrimonium halide, benzethonium halide, behenalkonium halide, cetalkonium halide, cetethyldimonium halide, cetylpyridinium halide, benzododecinium halide, chlorallyl methenamine halide, myristalkonium halide, stearalkonium halide or a mixture of two or more thereof, halide being preferably chloride or bromide, cationic lipids, amino alcohols, biguanide salts selected from the group comprising or consisting of chlorhexidine and salts thereof, polyaminopropyl biguanide, phenformin, alkylbiguanide or a mixture of two or more thereof, cationic compounds selected from 1,2-dioleyl-3-trimethyl-ammoniumpropane, 1,2-dioleoyl-sn-glycerophosphatidyl-ethanolamine, cationic glycosphingo-lipids or cationic cholesterol derivatives and any combinations thereof. Examples of anionic surfactants that are suitable for use in the present invention include, but are not limited to, lecithin, bile salts, fatty acids, and any combinations thereof.

In certain embodiments, the average hydrophilic-lipophilic balance (HLB) of the surface-active agent(s) is of the order of the required HLB or average HLB (RLHB) of the oil or oils of the oil phase used for the preparation of a pre-concentrate. Preferably, the RLHB value of the oil(s) of the oil phase and the HLB value of the surface-active agent(s) are substantially equal. As used herein, the term "hydrophilic-lipophilic balance or HLB" has its art understood meaning. When used in reference to a surfactant, it refers to a measure of the degree to which the surfactant is hydrophilic or lipophilic, determined by calculating values for the different regions of the molecule. The meaning of HLB value and RHLB value is discussed, for example, in "*Encyclopedia of Emulsion Technology*", P. Becher (Ed.), 1983, Marcel Dekker, 1: 217-220, which is incorporated herein by reference in its entirety.

In certain embodiments, the oil phase used in the preparation of a pre-concentrate according to the present invention, further comprises at least one pharmaceutically active substance or a prodrug. Preferably, pharmaceutically active substances (or prodrugs) are soluble in the oil phase.

Examples of pharmaceutically active substances or prodrugs that can be used in the practice of the present invention include, but are not limited to, antibiotics (e.g., aminoglycosides, carbacephem, carbapenems, macrolides, cephalosporins, glycopeptides, penicillins, polypeptides, quinolones, sulfonamides, tetracyclines and the like); antiviral agents (e.g., cidofovir, ganciclovir, valaciclovir or acyclovir); antifungals (e.g., polyene antibiotics, imidazole and triazole, allylamines); intraocular pressure lowering agents (e.g., alpha-adrenergic agonists, beta-adrenergic blockers, carbonic anhydrase inhibitors, cannabinoids, derivatives and prodrugs); anti-inflammatory agents including non-steroidal anti-inflammatory agents (e.g., COX-2 inhibitors, salicylates, 2-arylpropionic acids, N-arylanthranilic acids, oxicams, sulphonanilides, pyrazolidines derivatives, arylalkanoic acids, 3-benzolphenylacetic acids and derivatives); steroids (e.g., cortisone, hydrocortisone, prednisone, prednisolone, methylprednisone, fluorometholone, medrysone, betamethasone, loteprednol, flumethasone, mometasone, testosterone, methyltestosterone, danazol, beclomethasone, dexamethasone, dexamethasone palmitate, tramcinolone, triamcinolone acetonide, fluocinolone, fluocinolone acetonide, difluprednate); anti-allergic compounds (e.g., olapatadine, ketotifen, azelastine, epinastine, emedastine, levocabastive, terfenadine, astemizole and loratadine); anti-angiogenic compounds (e.g., thalidomide, VEGF inhibitors, VEGF soluble receptors, VEGF-traps, VEGF-antibodies, VEGF-traps, anti VEGF-siRNA); biological agents (e.g., antibodies or antibodies fragments, oligoaptamers, aptamers and gene fragments, oligonucleotides, plasmids, ribozymes, small interference RNA, nucleic acid fragments, peptides and antisense sequences); growth factors (e.g., epidermal growth factor, fibroblast growth factor, platelet derived growth factor, transforming growth factor beta, ciliary neurotrophic growth factor, glial derived neurotrophic factor, NGF, EPO and P1GF); immuno-modulating agents (e.g., qlucocorticoids, drugs acting on immunophilins, interferons, opioids); cytostatics (e.g., alkylating agents, anti-metabolites and cytotoxic antibiotics); antioxidants (e.g., alpha-tocopherol ascorbic acid, retinoic acid, lutein and their derivatives, precursors or prodrugs); UV-filter compounds (e.g., benzophenones); anti-redness agents (e.g., naphazoline, tetrahydrozoline, ephedrine and phenylephrine); fatty acids (e.g., omega-3 fatty acids), and the like, and any combinations thereof.

In certain embodiments, the pharmaceutically active substance is a non-steroidal anti-inflammatory agent, e.g., flubiprofen.

Other examples of pharmaceutically active substances or prodrugs that can be used in the practice of the present invention include, but are not limited to, anti-glaucomateaous active substances that can be selected among beta-blockers (e.g., levobunolol, befundol, metipranolol, forskolin, cartrolol, timolol); inhibitors of carbonic anhydrase (e.g., brinzolamide, dorzolamide, acetazolamide, methazolamide, dichlorophenamide); sympathomimetics (e.g., brimonidine, apraclonidine, dipivefrine, epinephrine); parasympathomimetics (e.g., pilocarpine); or cholinesterase inhibitors (e.g., physostigmine, echothiophate and/or their derivatives and/or pharmaceutically acceptable salts thereof).

Other examples of pharmaceutically active substances or prodrugs that can be used in the practice of the present invention include, but are not limited to, prostaglandins, preferably prostaglandin $F_{2\alpha}$ analogs such as, for example, latanoprost, unoprostone isopropyl, travoprost, bimatoprost, tafluprost, 8-isoprostaglandin E2, or any combination thereof. For example, the pharmaceutically active substance may be latanoprost.

Other examples of pharmaceutically active substances or prodrugs that can be used in the practice of the present invention include, but are not limited to, corticosteroids and prodrugs thereof that are suitable for ophthalmic use. Examples of corticosteroids include, but are not limited to, betamethasone, budenoside, cortisone, dexamethasone, hydrocortisone, methylprednisoline, prednisolone, prednisone, and triamcinolone. In certain embodiments, the oil phase used to prepare a pre-concentrate according to the present invention comprises a prodrug of a corticosteroid, for example a prodrug of dexamethasone, e.g., dexamethasone palmitate.

The amount of pharmaceutically active substance(s) included in the oil phase is generally such that the amount of active substance(s) in the final, oil-in-water ophthalmic emulsion is comprised between about 0.001% and 3%.

In certain embodiments, pre-concentrates prepared according to a process of the present invention comprise droplets having a mean size greater than about 10 nm and less than about 500 nm, preferably less than about 300 nm or less than about 200 nm. In certain preferred embodiments, the mean size of droplets in an inventive pre-concentrate is substantially the same as the mean size of droplets in the ophthalmic oil-in-water emulsion prepared therefrom.

In certain embodiments, pre-concentrates prepared according to a process of the present invention are stable over periods of time in excess of 24 hours, preferably in excess of 3 days, more preferably in excess of 7 days.

Pre-concentrates prepared according to processes of the present invention may be under any form that is suitable for its further dilution in an aqueous medium. Thus, in certain embodiments, a pre-concentrate of the invention is in a liquid form. In other embodiments, a pre-concentrate is in a gel form.

A pre-concentrate of the invention is in the form of an emulsion, which may be a cationic emulsion (i.e., a composition comprising colloid particles having a positive zeta potential), an anionic emulsion (i.e., a composition comprising colloid particles having a negative zeta potential), or a non-ionic emulsion (i.e., a composition comprising colloid particles having a zeta potential null). As known in the art, the zeta potential is a measure of the magnitude of repulsion or attraction between particles The zeta potential is not measurable directly but it can be calculated using theoretical models and an experimentally-determined electrophoretic mobility or dynamic electrophoretic mobility. As known in the art, electrophoretic mobility can be determined using micro-electrophoresis or electrophoretic light scattering. In certain preferred embodiments, a pre-concentrate is preferably in the form of a cationic emulsion.

In many embodiments, pre-concentrates produced by processes of the present invention are not suitable for administration to the eye of a subject, but becomes suitable for ophthalmic use after dilution with an aqueous medium.

B. Ophthalmic Oil-in-Water Emulsions and Preparation Thereof

The present invention also provides processes for the manufacture of ophthalmic oil-in-water emulsions. Such processes generally comprise steps of: manufacturing a pre-concentrate as described above; and diluting one volume of the pre-concentrate with between 2 and 50 volumes of a diluting aqueous solution, for example between 2 and 25 volumes, or between 2 and 10 volumes. As disclosed above, pre-concentrates used in such processes have a content in oil of between about 3% and about 50% v/v, e.g., between about 6% and about 30% v/v or between about 10% and about 20% v/v; and comprise at least one oil that is suitable for use in ophthalmic applications.

In certain embodiments, the diluting aqueous phase comprise one or more additives selected from the group consisting of emulsifying agents, suspending agents, dispersing or wetting agents, tonicity agents, viscosifying agents, buffering agents, preservatives, chelating agents, anti-foaming agents, antioxidants, colorants, and any combinations thereof.

Examples of emulsifying agents are naturally occurring gums, naturally occurring phosphatides (e.g., soybean lecithin, sorbitan mono-oleate derivatives), sorbitan esters, mono glycerides, fatty alcohols (e.g., cetyl alcohol, oleyl alcohol), and fatty acid esters (e.g., triglycerides of fatty acids, sodium cetostearyl sulfate). Emulsifying agents may be present at a concentration between about 0.01% and about 1% w/w. In this section, percentages are given in weight/weight (w/w) of the final emulsion.

Examples of buffering agents include citric acid, acetic acid, lactic acid, hydrogenophosphoric acid, diethylamine, sodium hydroxide and tromethane (i.e., tris-(hydroxymethyl) aminomethane hydrochloride). Buffering agents may be present at a concentration between about 5 nM and about 100 m.

Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans. Suspending agents may be present at a concentration between about 0.1% to about 15% w/w.

Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate). Dispersing or wetting agents may be present at a concentration between about 0.001% to about 5% w/w.

Examples of tonicity agents include, but are not limited to, NaCl, glycerol and mannitol. Tonicity agents may be present at a concentration between about 0.1% to about 5% w/w.

Preservatives may be added to a composition of the invention to prevent microbial contamination that can affect the stability of the formulation and/or cause infection in the patient. Suitable examples of preservatives include chlorexidine, polyoxyethylen biguenide, parabens (such as methyl, ethyl, propyl, p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol. Preservatives may be present at a concentration between about 0.0001% and about 0.02% w/w.

Examples of chelating agents include sodium EDTA and citric acid. Chelating agents may be present at a concentration between about 0.001% and about 0.1% w/w.

Anti-foaming agents usually facilitate manufacture of compositions, they dissipate foam by destabilizing the air-liquid interface and allow liquid to drain away from air pockets. Examples of anti-foaming agents include simethicone, dimethicone, ethanol, and ether. Anti-foaming agents may be present at a concentration between about 0.1% and about 5% w/w.

Examples of gel bases or viscosity-increasing agents are liquid paraffin, polyethylene, fatty oils, colloidal silica or aluminum, glycerol, propylene glycol, propylene carbonate, carboxyvinyl polymers, magnesium-aluminum silicates, hydrophilic polymers (such as, for example, starch or cellulose derivatives), water-swellable hydrocolloids, carragenans, hyaluronates, alginates, and acrylates. Gel bases and viscosity-increasing agents may be present at a concentration between about 0.5% and about 10% w/w.

In certain embodiments, a diluting aqueous solution used in a process of the present invention, alternatively or additionally, comprises benzalkonium chloride. Benzalkonium chloride, a nitrogenous cationic surface-acting agent belonging to the family of quaternary ammonium compounds, is the most commonly used preservative in opthalmology. Benzalkonium chloride also has cationic agent properties, and is used as cationic agents for emulsions, especially ophthalmic emulsions.

Benzalkonium chloride, as usually provided by the manufacturers wanting to comply with the European and/or American Pharmacopeia, is a mixture of n-alkyl dimethyl benzyl ammonium chlorides of various alkyl chain lengths. For example, FeF Chemicals A/S (Denmark) supplies, under reference 8100301U (BAK USP/NF), a mixture of three alkyl dimethyl benzyl ammonium chlorides including: (1) 60-70% of $C_{12}$-alkyl dimethyl benzyl ammonium chloride (2) 30-40% of $C_{14}$-alkyl-1 dimethyl benzyl ammonium chloride, and less than 5% of $C_{16}$-alkyl dimethyl benzyl ammonium chloride. BAK may be present at a concentration between about 0.005% and about 0.02% w/w.

In certain embodiments, the diluting aqueous phase comprises, alternatively or additionally, at least one water-soluble therapeutic agent. Suitable water-soluble therapeutic agents may be found in a wide variety of classes of drugs including, but not limited to, analgesics, anesthetics, relaxants, hormones, anti-inflammatory agents, vitamins, minerals, anti-angiogenic agents, wound healing agents, cytokines, growth factors, anti-histaminic agents, anti-bacterial agents, anti-viral agents, antibiotics, antipruritic agents, antipyretic agents, and the like.

Ophthalmic oil-in-water emulsions prepared according to processes provided herein generally have a content in oil of 5% v/v or less, preferably of 3% v/v or less, more preferably of 2% v/v or less, even more preferably of 1% v/v or less. They generally contain droplets having a mean size greater than about 10 nm and less than about 500 nm, preferably less than about 300 nm or less than about 200 nm. In certain preferred embodiments, the mean size of droplets in an inventive oil-in-water emulsion is substantially the same as the mean size of droplets in the pre-concentration from which it is prepared by dilution. In preferred embodiments, an inventive oil-in-water emulsion is stable over a period of time greater than about 12 months, preferably greater than about 24 months, or more preferably greater than about 36 months.

II—Pharmaceutical Compositions of Ophthalmic Oil-in-water Emulsions

Ophthalmic oil-in-water emulsions described herein may be administered per se or in the form of a pharmaceutical composition. Accordingly, the present invention provides pharmaceutical compositions comprising an effective amount of an oil-in-water emulsion described herein and at least one pharmaceutically acceptable carrier, vehicle or excipient. As will be recognized by one skilled in the art, pharmaceutically acceptable carriers or excipients may be included in the diluting aqueous phase used in the preparation of the emulsion from an inventive pre-concentrate.

Pharmaceutical compositions of the present invention may be in the form of liquid or semi-solid dosage preparations. For example, they may be formulated as emulsions, lotions, liniments, jellies, ointments, creams, pastes, gels, hydrogels, aerosols, sprays, foams, and the like.

The inventive pharmaceutical compositions may be prepared according to general pharmaceutical practice (see, for example, "Remington's Pharmaceutical Sciences", E. W. Martin, 18$^{th}$ Ed., 1990, Mack Publishing Co.: Easton, Pa. and "Encyclopedia of Pharmaceutical Technology", 1988, J. Swarbrick, and J. C. Boylan (Eds.), Marcel Dekker, Inc: New York, each of which is incorporated herein by reference in its entirety).

Pharmaceutically acceptable carriers, vehicles, and/or excipients suitable for incorporation into compositions of the present invention can be routinely selected for a particular use by those skilled in the art. Such carriers, vehicles and excipients include, but are not limited to, solvents, buffering agents, inert diluents, suspending agents, dispersing agents or wetting agents, preservatives, stabilizers, chelating agents, emulsifying agents, anti-foaming agents, gel-forming agents, humectants, and the like. Excipient characteristics that are considered include, but are not limited to, the biocompatibility and biodegradability at the site of administration, compatibility with pharmaceutically active substances present, and processing conditions, such as temperature, pressure, and the like.

In certain embodiments of the present invention, pharmaceutical compositions are formulated to provide a local controlled release of one or more components of the composition. Any pharmaceutically acceptable carrier, vehicle or excipient suitable for administration to the eye may be employed. Examples of slow release formulation include polymer formulations (such as vesicles or liposomes) and microparticles (such as microspheres or microcapsules).

A wide variety of biodegradable materials may be used to provide controlled release of one or more components of compositions of the present invention. The controlled release material should be biocompatible and be degraded, dissolved or absorbed in situ in a safe and pharmaceutically acceptable manner so that the material is removed from the site of administration by natural tissue processes and in a suitable amount of time. The controlled release carrier should not cause any unwanted local tissue reaction or induce systemic or local toxicity.

Suitable controlled release biodegradable polymers for use in the formulation of compositions of the invention may comprise polylactides, polyglycolides, poly(lactide-co-glycolides) polyanhydrides, polyorthoesters, polycaprolactones, polysaccharides, polyphosphazenes, proteinaceous polymers and their soluble derivatives (such as gelation biodegradable synthetic polypeptides, alkylated collagen, and alkylated elastin), soluble derivatives of polysaccharides, polypeptides, polyesters, and polyorthoesters.

The pharmacokinetic release profile of these formulations may be first order, zero order, bi- or multi-phasic, to provide the desired therapeutic effect over the desired period of time. A desired release profile can be achieved by using a mixture of polymers having different release rates and/or different percent loadings of a pharmaceutically active substance. Methods for the manufacture of liposomes, microspheres and microcapsules are well known in the art.

Pharmaceutical compositions of the present invention may be formulated in dosage unit form for ease of administration and uniformity of dosage. The expression "unit dosage form", as used herein, refers to a physically discrete amount of an emulsion to treat a patient. It will be understood, however, that the total daily dose of compositions of the present invention will be decided by the attending physician within the scope of sound medical judgment.

In certain embodiments, compositions of the present invention are combined with, coated on, or incorporated within a device that can be applied to the eye, e.g., an ocular lens.

A pre-concentrate and/or the resulting oil-in-water emulsion may be sterilized using any suitable method including, but not limited to, by heat, such as by autoclaving, or by filtering or filtration, or by irradiation, or by gas sterilization. In certain embodiments, the pre-concentrate is prepared under aseptic conditions. In other embodiments, the final oil-in-water emulsion is sterilized following the dilution step. In yet other embodiments, dilution is performed under aseptic conditions. In certain embodiments, a pharmaceutical composition to be administered to the eye of a subject is sterile.

III—Indications and Administration

In another aspect, the present invention relates to methods for the treatment of eye diseases or conditions. Such methods generally comprise a step of administering to a subject in need thereof, an effective amount of an ophthalmic oil-in-water emulsion obtained by a process disclosed herein.

Administration may be by any suitable method, including topical administration, intraocular administration, and periocular administration.

Eye diseases or conditions that can be treated using emulsions and methods of the present invention may be any of a wide variety of ocular conditions such as glaucoma, ocular inflammatory conditions such as keratitis, uveitis, intra-ocular inflammation, post-surgery inflammation, allergy and dry-eye syndrome ocular infections, ocular allergies, ocular infections, cancerous growth, neo vessel growth originating from the cornea, retinal oedema, macular oedema, diabetic retinopathy, retinopathy of prematurity, degenerative diseases of the retina (macular degeneration, retinal dystrophies), and retinal diseases associated with glial proliferation.

A treatment according to the present invention may consist of a single dose or a plurality of doses over a period of time. Administration may be one or multiple times daily, weekly (or at some other multiple day interval) or on an intermittent schedule.

Optimization of the appropriate dosages can readily be made by one skilled in the art in light of pharmacokinetic data observed in clinical trials. Final dosage regimen will be determined by the attending physician, considering various factors which modify the action of the drug, e.g., the drug's specific activity, the severity of the disease or condition and the responsiveness of the patient, the age, condition, body weight, sex and diet of the patient, the severity of any present infection, time of administration, the use (or not) of concomitant therapies, and other clinical, factors.

It will be appreciated that pharmaceutical compositions of the present invention can be employed alone or in combination with additional therapies. In other words, a treatment according to the present invention can be administered concurrently with, prior to, and/or following one or more desired therapeutics or medical procedures. The particular combination of therapies (therapeutics or procedures) to employ in such combination regimen will take into account compatibility of the desired therapeutics and/or procedures and the desired therapeutic effect to be achieved.

For example, a pharmaceutical composition of the present invention may be administered to a subject following eye surgery. Examples of eye surgery procedures include, but are not limited to, laser surgery; cataract surgery; glaucoma surgery (e.g., canaloplasty); refractive surgery (e.g., keratomilleusis, automated lamellar keratoplasty, Laser assisted in situ keratomileusis or LASIK, photorefractive keratectomy, laser thermal keratoplasty, conductive keratoplasty, and astigmatic keratotomy); corneal surgery (e.g., corneal transplant surgery, penetrating keratoplasty, and phototherapeutic keratectomy); vitréo-retinal surgery (e.g., vitrectomy, retinal detachment repair, and macular hole repair); eye muscle surgery; oculoplastic surgery; eyelid surgery; orbital surgery; and other opthalmologic surgery procedures.

IV—Pharmaceutical Packs or Kits

In another aspect, the present invention relates to pharmaceutical packs or kits. A pharmaceutical pack or kit according to the present invention comprises one or more containers (e.g., vials, ampoules, test tubes, flasks, bottles, or pre-filled syringes) containing one or more ingredients of an inventive composition, allowing administration of the composition to a subject. Such containers may be made of glass, plastic materials, resins, and the like. They may be transparent or, alternatively, they may be colored or opaque to prevent or reduce the risk that active ingredients be directly exposed to light. In certain embodiments, a container is in a form that allows for administration of a controlled volume (e.g., a drop) of an inventive composition. In other embodiments, a container comprises a system (e.g., a dropper) allowing administration of a controlled volume of an inventive composition.

Different ingredients of a pharmaceutical pack or kit may be supplied in a liquid form or in a solid form (e.g., lyophilized). Each ingredient will generally be suitable as aliquoted in its respective container or provided in a concentrated form. Pharmaceutical packs or kits may include media for the reconstitution of lyophilized ingredients. Individual containers of a kit will preferably be maintained in close confinement for commercial sale.

In certain embodiments, a pharmaceutical pack or kit includes one or more additional approved therapeutic agents as described above. Optionally associated with such container(s) can be a notice or package insert in the form prescribed by a governmental agency regulating the manufacture, use or sale of pharmaceutical or biological, products, which notice reflects approval by the agency of manufacture, use or sale for human administration. The notice or package insert may contain instructions for use of a pharmaceutical composition according to methods disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Preparation of One Batch of 100 kg of an Emulsion Comprising Cyclosporine A

1—Composition

The following table presents the composition of the Cyclosporine A emulsion.

|  | Chemical name ingredient | Quantity % (w/w) | Unit formula Quantity in mg for a 300 µL single use vial | Batch formula Quantity in g for a 100 kg batch |
|---|---|---|---|---|
| Oily phase | Excipients: | | | |
|  | MCT | 2.00 | 6.00 | 2 000 |
|  | Tyloxapol | 0.30 | 0.90 | 300 |
|  | Active ingredient: | | | |
|  | Ciclosporin A | 0.10 | 0.30 | 100 |
|  | Total | 2.40 | 7.20 | 2 400 |
| Aqueous phase | Excipients: | | | |
|  | Poloxamer 188 | 0.10 | 0.30 | 100 |
|  | Glycerin | 2.25 | 6.75 | 2 250 |
|  | BAK | 0.02 | 0.06 | 20 |
|  | WFI | 95.23 | 285.69 | 95 230 |
|  | Total | 97.60 | 292.80 | 97 600 |

-continued

| Chemical name ingredient | Quantity % (w/w) | Unit formula Quantity in mg for a 300 μL single use vial | Batch formula Quantity in g for a 100 kg batch |
|---|---|---|---|
| Excipients used during production: | | | |
| Sodium hydroxide 0.1N | QS pH 7.0 ± 0.5 | QS pH 7.0 ± 0.5 | QS pH 7.0 ± 0.5 |
| Nitrogen | / | / | / |

2—Compounding Process

Figure 1:
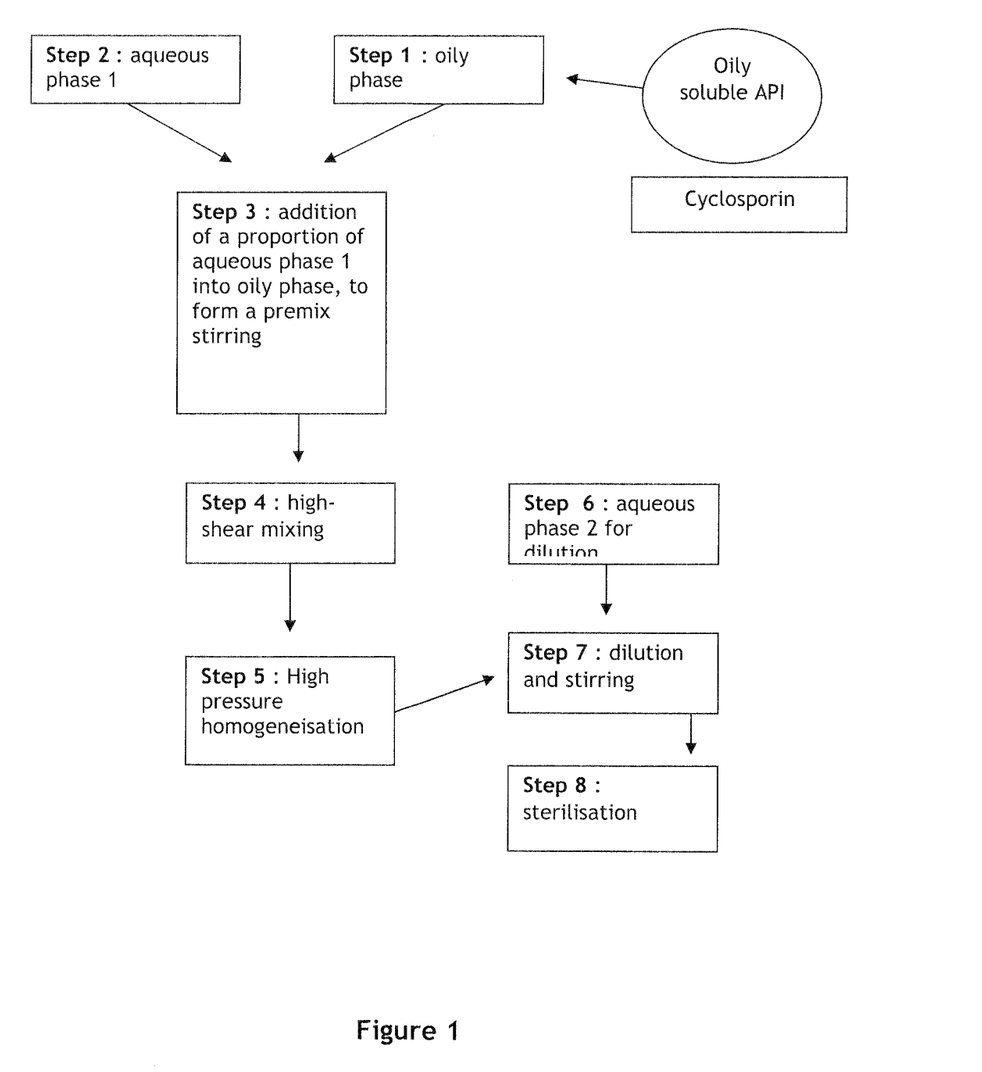
FIG. 1 is a scheme showing the compounding process using in the preparation of the emulsion of cyclosporine A as described in Example 1.

FIG. 1 presents a scheme of the compounding process used in the preparation. In steps 1, 2, and 6, each phase was prepared separately including the API in the oily phase. The aqueous phase and oil phase obtained in steps 1 and 2 were then then diluted to get a premix (w/w) in step 3. The resulting premix was submitted to a high-shear mixing for about, 30 minutes to 1 hour (Step 4), and then homogenized under high pressure for about 5 hours (Step 5). A second dilution was then performed (Step 6 and 7) in a ratio of 1 w premix/6 w aqueous phase 2, to obtain the final emulsion, which was then sterilized by heating (Step 8).

3—Results

The following table presents the results of partial controls performed according to the mentioned procedure.

| Chemicals controls | Ref method | Specifications |
|---|---|---|
| pH | Ph Eur 2.2.3 | 4.5-6.5 |
| Sterilty | Ph Eur 2.6.1 | Sterile |
| Zeta potential | Internal monograph | Positive |
| Mean oil droplets size | Internal monograph | 100-300 nm |

Example 2

Preparation of One Batch of 500 kg of an Emulsion that does not Comprise API

1—Composition

The following table presents the composition of the Cyclosporine A emulsion.

| | Chemical name ingredient | Quantity % (w/w) | Unit formula Quantity in mg for a 400 μL single use vial | Batch formula Quantity in g for a 500 kg batch |
|---|---|---|---|---|
| Oily phase | Excipients: | | | |
| | Heavy mineral oil | 0.500 | 2.000 | 2 500 |
| | Light mineral oil | 0.500 | 2.000 | 2 500 |
| | Tyloxapol | 0.300 | 1.200 | 1 500 |
| | Cationic agent | 0.002 | 0.008 | 10 |
| | Total | 1.302 | 5.208 | 6 510 |
| Aqueous phase | Excipients: | | | |
| | Poloxamer 188 | 0.100 | 0.400 | 500 |
| | Mannitol | 3.300 | 13.200 | 16 500 |
| | Tromethamine | 0.006 | 0.024 | 30 |
| | Tris hydrochloride | 0.071 | 0.284 | 355 |
| | WFI | 95.221 | 380.884 | 476 105 |
| | Total | 98.698 | 394.792 | 493 490 |
| Nitrogen | | / | / | / |

2—Compounding Process

Figure 2:
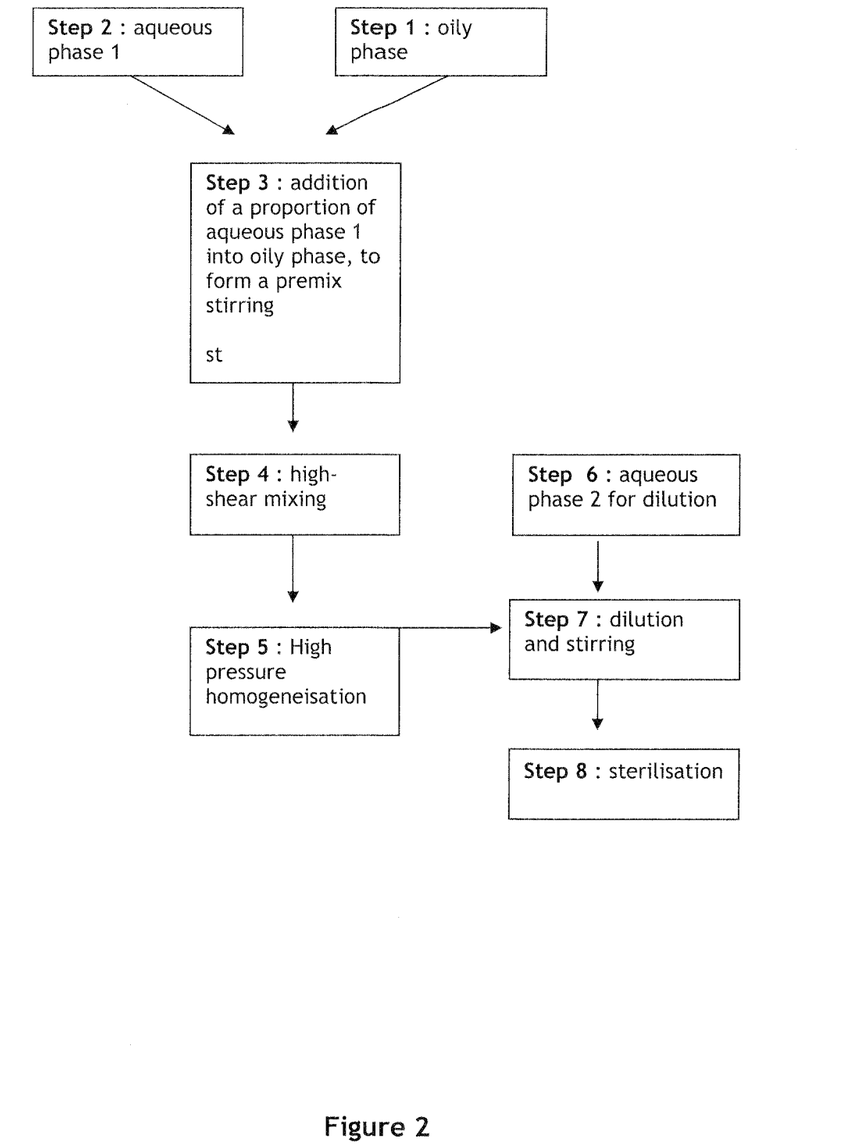
FIG. 2 is a scheme showing the compounding process using in the preparation of an emulsion that does not comprise API, as described in Example 2.

FIG. 2 presents a scheme of the compounding process used in the preparation. In steps 1, 2 and 6, each phase was prepared separately. The aqueous phase and oil phase obtained in steps 1 and 2 were then diluted to get a premix (w/w) in step 3. The resulting premix was submitted to a high-shear mixing for about 1 hour (Step 4), and then homogenized under high pressure for about 8 hours (Step 5). A second dilution was then performed (Step 6 and 7) in a ratio of 1 w premix/10 w aqueous phase 2, to obtain the final emulsion, which was then sterilized by heating (Step 8).

3—Results

The following table presents the results of partial controls performed according to the mentioned procedure.

| Chemicals controls | Ref method | Specifications |
|---|---|---|
| pH | Ph Eur 2.2.3 | 6.0-8.0 |
| Sterilty | Ph Eur 2.6.1 | Sterile |
| Zeta potential | Internal monograph | Positive |
| Mean oil droplets size | Internal monograph | 100-300 nm |

Example 3

Preparation of One Batch of 100 kg of an Emulsion Comprising Naphazolin

1—Composition

The following table presents the composition of the Naphazolin emulsion.

| Chemical name ingredient | | Quantity % (w/w) | Unit formula Quantity in mg for a 300 µL single use vial | Batch formula Quantity in g for a 100 kg batch |
|---|---|---|---|---|
| Oily phase | Excipients: | | | |
| | Castor oil | 1.000 | 3.000 | 1 000 |
| | Tyloxapol | 0.300 | 0.900 | 300 |
| | Propylene glycol | 1.000 | 3.000 | 1 000 |
| | Total | 2.300 | 6.900 | 2 300 |
| Aqueous phase | Excipients: | | | |
| | Poloxamer 188 | 0.100 | 0.300 | 100 |
| | Glycerin | 2.250 | 6.750 | 2 250 |
| | Cationic agent | 0.008 | 0.024 | 8 |
| | WFI | 95.312 | 285.936 | 95 312 |
| | Active ingredient: | | | |
| | Naphazolin | 0.030 | 0.090 | 30 |
| | Total | 97.700 | 293.100 | 97 700 |
| Excipients used during production: | | | | |
| Sodium hydroxide 0.1N | | QS pH 6.0 ± 1 | QS pH 6.0 ± 1 | QS pH 6.0 ± 1 |
| Nitrogen | | / | / | / |

2—Compounding Process

Figure 3:
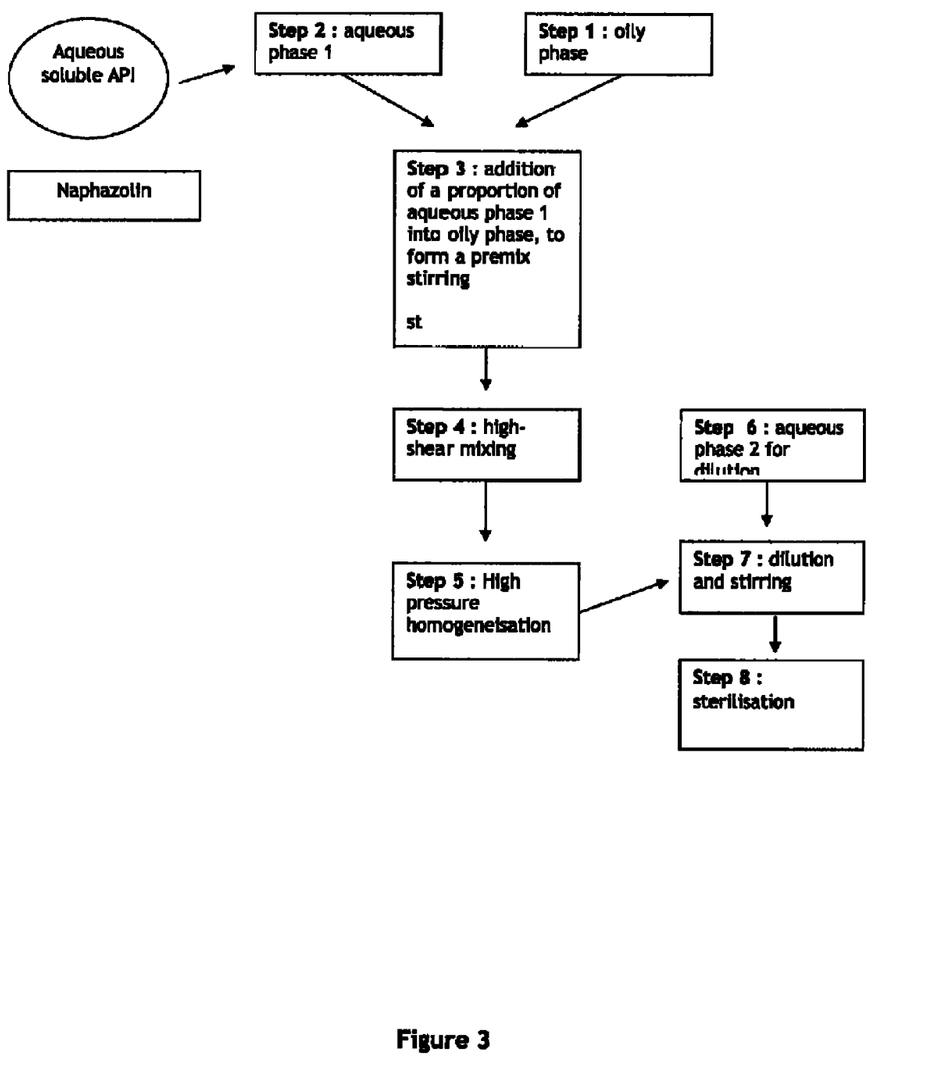
FIG. 3 is a scheme showing the compounding process using in the preparation of an emulsion of Naphazolin, as described in Example 3.

FIG. 3 presents a scheme of the compounding process used in the preparation. In steps 1, 2 and 6, each phase was prepared separately. The API was included in the aqueous phase. The aqueous phase and oil phase obtained in steps 1 and 2 were then diluted to get a premix (w/w) in step 3. The resulting premix was submitted to a high-shear mixing for about 30 minutes (Step 4), and then homogenized under high pressure for about 5 hours (Step 5). A second dilution was then performed (Step 6 and 7) in a ratio of 1 w premix/25 w aqueous phase 2, to obtain the final emulsion, which was then sterilized by heating (Step 8).

3—Results

The following table presents the results of partial controls performed according to the mentioned procedure.

| Chemicals controls | Ref method | Specifications |
|---|---|---|
| pH | Ph Eur 2.2.3 | 5.0-7.0 |
| Sterilty | Ph Eur 2.6.1 | Sterile |
| Zeta potential | Internal monograph | Negative |
| Mean oil droplets size | Internal monograph | 225 ± 75 nm |

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A process for manufacturing a cationic ophthalmic oil-in-water emulsion, said process comprising steps of:
   manufacturing a pre-concentrate of a cationic ophthalmic oil-in-water emulsion, said manufacturing comprising a step of emulsifying an oil phase with an aqueous phase and at least one surface-active agent to obtain the pre-concentrate, wherein the oil phase comprises at least one oil suitable for ophthalmic use, and wherein the pre-concentrate obtained is a cationic emulsion having a content in oil of between 6% and 50% v/v; and
   diluting one volume of the pre-concentrate with between 2 and 50 volumes of a diluting aqueous solution,
   wherein said emulsifying step comprises using a device selected from the group consisting of a colloid mill, a rotor/stator homogenizer, a high pressure homogenizer, and a sonicating homogenizer to obtain said emulsion,
   wherein the at least one surface-active agent is tyloxapol.

2. The process of claim 1, wherein the pre-concentrate has a content in oil of between 6% and 30% v/v.

3. The process of claim 1, wherein the pre-concentrate has a content in oil of between 10% and 20% v/v.

4. The process of claim 1, wherein the oil suitable for ophthalmic use is selected from the group consisting of castor oil, medium chain triglycerides, mineral oils, vegetal oils, and any combination thereof.

5. The process of claim 1, wherein the oil phase further comprises at least one pharmaceutically active substance.

6. The process of claim 5, wherein the pharmaceutically active substance is selected from the group consisting of antibiotics, antiviral agents, antifungals, intraocular pressure lowering agents, anti-inflammatory agents, steroids, anti-allergic compounds, anti-angiogenic compounds, antibodies and fragments thereof, oligoaptamers, aptamers and gene fragments, oligonuicleotides, plasmids, ribozymes, small interference RNA, nucleic acid fragments, peptides and antisense sequences, growth factors, immunomodulating agents, drugs acting on immunophilins, interferons, opioids, cytostatics, antioxidants, UV-filter compounds, anti-redness agents, omega-3 fatty acids, prodrugs thereof, and any combination thereof.

7. The process according to claim 5 wherein the pharmaceutically active substance is selected from the group consisting of cyclosporine A, latanoprost, dexamethasone palmitate, and flubiprofen.

8. The process according to claim 1, wherein the pre-concentrate obtained comprises droplets having a mean size of more than about 10 nm and less than about 500 nm.

9. The process of claim 1, wherein the pre-concentrate is stable for a period of time exceeding at least 24 hours.

10. The process according to claim 1, wherein the diluting aqueous solution comprises an additive selected from the group consisting of tonicity agents, viscosifying agents, buffering agents, preservatives, antioxidants, colorants, micellar solutions, and combinations thereof.

11. The process according to claim 1, wherein the diluting aqueous solution comprises benzalkonium chloride.

12. The process according to claim 1, wherein the diluting aqueous solution comprises at least one water-soluble therapeutic agent.

13. The process according to claim 12, wherein the water-soluble therapeutic agent is a water-soluble member of the group consisting of analgesics, anesthetics, relaxants, hormones, anti-inflammatory agents, vitamins, minerals, anti-angiogenic agents, wound healing agents, cytokines, growth factors, anti-histaminic agents, anti-bacterial agents, anti-viral agents, antibiotics, antipruritic agents, antipyretic agents, and the like.

14. The process according to claim 1, wherein the oil-in-water emulsion comprises droplets having a mean size of more than about 10 nm and less than about 500 nm.

15. The process according to claim 1, wherein the oil-in-water emulsion is stable for a period of time exceeding at least about 12 months.

16. An ophthalmic oil-in-water emulsion obtained by the process of claim 1.

17. A pharmaceutical composition comprising an effective amount of an ophthalmic oil-in-water emulsion of claim 16.

18. A method for treating an eye disease or condition in a subject, the method comprising a step of: administering to said subject an effective amount of an ophthalmic oil-in-water emulsion of claim 16.

19. The method of claim 18, wherein the eye disease or condition is a member of the group consisting of inflammation, allergy, dry eye, retinal diseases, infections, glaucoma, and ocular hypertension.

20. The process according to claim 1, wherein the pre-concentrate obtained comprises droplets having a mean size of more than about 10 nm and less than 200 nm.

21. The process according to claim 1, wherein the pre-concentrate is stable for a period of time exceeding at least 3 days.

22. The process according to claim 1, wherein the pre-concentrate is stable for a period of time exceeding at least 7 days.

23. The process according to claim 1, wherein the oil-in-water emulsion comprises droplets having a mean size of more than about 10 nm and less than 200 nm.

24. The process according to claim 1, wherein the oil-in-water emulsion is stable for a period of time exceeding at least about 24 months.

25. The process according to claim 1, wherein the oil-in-water emulsion is stable for a period of time exceeding at least about 36 months.

* * * * *